United States Patent [19]
Clayton

[11] 4,206,224
[45] Jun. 3, 1980

[54] TREATMENT OF INFECTIONS

[75] Inventor: John P. Clayton, Horsham, England

[73] Assignee: Beecham Group Limited, Great Britain

[21] Appl. No.: 924,493

[22] Filed: Jul. 14, 1978

Related U.S. Application Data
[62] Division of Ser. No. 842,399, Oct. 17, 1977.

[30] Foreign Application Priority Data
Oct. 23, 1976 [GB] United Kingdom .............. 44133/76

[51] Int. Cl.² .............................................. A61K 31/35
[52] U.S. Cl. .................................................. 424/283
[58] Field of Search ......................................... 424/283

[56] References Cited
FOREIGN PATENT DOCUMENTS
1395907  5/1975  United Kingdom .................... 424/283

Primary Examiner—Jerome D. Goldberg
Attorney, Agent, or Firm—Jacobs & Jacobs

[57] ABSTRACT

Pseudomonic acid of formula (I):

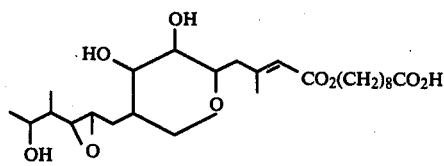

is effective against *H. influenzae, N. gonorrhoeae,* and Mycoplasma sp organisms and is therefore of value in the treatment of respiratory, venereal and mycoplasma-induced diseases.

9 Claims, No Drawings

TREATMENT OF INFECTIONS

CROSS-REFERENCE

This is a division of Ser. No. 842,399 filed Oct. 17, 1977.

This invention relates to treatment of infections and in particular to the treatment of certain bacterial infections in mammals including man.

Pseudomonic acid is the E-isomer of the structure (I):

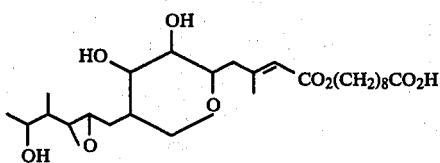

and is disclosed as having antibacterial activity in British Pat. No. 1,395,907. It has now been found that pseudomonic acid has particularly high activity against *Haemophilus influenzae, Neisseria gonorrhoeae* and *Mycoplosma sp*, and is therefore of value in the treatment of respiratory and veneral diseases, and of mycoplasma-induced human and veterinary diseases.

The present invention provides a method of treatment of respiratory, venereal, and mycoplasma-induced diseases in mammals, which method comprises the administration of an effective amount of pseudomonic acid of formula (I) or a nontoxic salt or ester thereof.

It is believed that pseudomonic acid has the absolute stereochemistry as shown in formula (IA):

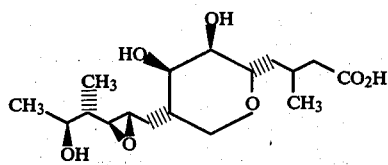

Suitable non-toxic salts of pseudomonic acid which may be administered include metal salts, e.g. aluminium, alkali metal salts such as sodium or potassium, alkaline earth metal salts such as calcium or magnesium, and ammonium or substituted ammonium salts for example those with lower alkylamino such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylene-diamine, 1-ephenamine, N-ethylpiperidine, N-benzyl-$\beta$-phenethyl-amine, dehydroabietylamine, N,N'-bis-dehydroabietylethylenediamine, or bases of the pyridine type such as pyridine, collidine or quinoline.

Preferred salts are alkali metal salts.

Suitable esters include alkyl, aryl and aralkyl groups, any of which may be substituted with a hydroxy, amino or halogen group. For example the ester group may be a $C_{1-6}$ alkyl group in particular, methyl, ethyl, n- or iso-propyl, n, sec-, iso or tert-butyl; a halo-($C_{1-6}$)-alkyl group such as trifluoromethyl, 2,2,2-trichloroethyl; an aminoalkyl group such as aminomethyl, 2-aminoethyl; hydroxymethyl, hydroxyethyl; phenyl; substituted phenyl; or a benzyl group.

Preferred esters are $C_{1-6}$ alkyl esters

The infections which pseudomonic acid, its salts and esters are particularly useful against include venereal disease. Because it is not a $\beta$-lactam antibiotic it is effective against $\beta$-lactamase strains of *N. gonorrhoeae*, for which penicillin and cephalosporin antibiotics would not be useful. Pseudomonic acid is also effective in the treatment of respiratory infections, such as chronic bronchitis and bacterial meningitis, non-specific urethritis and pneumonia. In animals it may be employed generally as a growth promoter, or for the treatment of mastitis in cattle and for treatment of mycoplasma infections in animals such as turkeys, chickens and pigs.

Some of the human and veterinary diseases caused by mycoplasma species, and against which pseudomonic acid, its salts and esters are effective, are as follows:

Avian
  *M. gallisepticum*—Chronic respiratory diseases (airsacculitis) of chicken and turkeys.
  *M. synoviae*—Airsacculitis and infections synovitis
Bovine
  *M. Bovis*—Mastitis, respiratory disease and arthritis of cattle
  *M. dispar*—Calf pneumonia
Porcine
  *M. suipneumoniae*—Enzootic pneumonia of pigs
Murine
  *M. Pulmonis*—pneumonia of rats and mice
  *M. pulmonis 'JB'*—also causes arthritis in mice
Human
  *M. pneumoniae*—primary atypical pneumonia
  *M. fermentans* MWK14 was isolated from a joint of a rheumatoid patient.

Pseudomonic acid is particularly useful in the treatment of enzootic pneumonia in animals such as pigs, calves and sheep, because it also has activity against the bacteria *Bordetella bronchiseptica* and *Pasteurella multocida*, both of which often cause respiratory complications in case of this disease.

Pseudomonic acid or a salt or ester thereof may be formulated in any convenient way for use in human or veterinary medicine.

The compositions may be formulated for administration by any route, and would depend on the disease being treated. The compositions may be in the form of tablets, capsules, powders granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl pyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired convention flavouring or colouring agents.

Suppositories will contain conventional suppository bases, e.g. cocoa butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability the composition can be frozen after filling into the vial and water removed under vacuum. The dry lypophilized powder is then sealed in the and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration. Where the compositions comprise dosage units, each unit will preferably contain from 50–500 mg., of the active ingredient. The dosage as employed for adult human treatment will preferably range from 100 mg to 3g., per day, for instance 250 mg-2g., per day, depending on the route and frequency of administration.

Alternatively, pseudomonic acid or a salt or ester may be administered as part of the total dietary intake. In this case the amount of compound employed may be less than 1% by weight of the diet and preferably no more than 0.5% by weight. The diet for animals may consist of normal foodstuffs to which the compound may be added or it may be added to a premix.

Biological Data

1. MIC values

Table 1 shows the antibacterial spectrum of pseudomonic acid. It has good activity against staphylococci and most streptococci. Gonococci and *Haemophilus influenzae* are very susceptible to the compound, including strains resistant to other antibiotics. Most mycoplasma species are also very sensitive to pseudomonic acid. The compound is relatively inactive against Gram-negative bacilli.

Table 1

| Antibacterial spectrum of Pseudomonic Acid | |
|---|---|
| Organism | MIC($\mu$g/ml) |
| *Staphylococcus aureus* | 0.25 |
| *Staphylococcus epidermidis* | 0.25 |
| *Streptococcus pyogenes* | 0.25 |
| *Streptococcus pneumoniae* | 0,12 |
| *Streptococcus faecalis* | 50 |
| *Haemophilus influenzae* | 0.12 |
| *Neisseria gonorrhoeae* | 0.01 |

Table 1-continued

| Antibacterial spectrum of Pseudomonic Acid | |
|---|---|
| Organism | MIC($\mu$g/ml) |
| *Neisseria meningitidis* | 0.02 |
| Mycoplasma species | <0.01–25 |
| Gram-negative bacilli | 50–>500 |

2. Blood Levels

The results of administering pseudomonic acid to four different animal species are shown in Table 2 in terms of peak blood levels and urinary recovery.

Table 2

| Animal Blood and Urinary Excretion Levels for Pseudomonic Acid | | | | |
|---|---|---|---|---|
| Species | Route | Dose mg/kg | Peak Level $\mu$g/ml | Urinary Recovery % |
| Mouse | p.o. | 50 | <1.0 | <1.0 |
| | s.c. | 50 | 7.2 | <1.0 |
| Rat | i.m. | 100 | 15.8 | <1.0 |
| | i.v. | 100 | 66.7 | <1.0 |
| Dog | p.o. | 100 | 3.6 | <1.0 |
| | i.m. | 100 | 25.3 | 1.0 |
| Squirrel | p.o. | 100 | 26.8 | 1.5 |
| Monkey | i.m. | 100 | 40.0 | 2.0 |

3. Toxicity

Pseudomonic acid appears to have a low degree of toxicity as shown in Table 3 which gives $LD_{50}$ values in the rat and mouse for three routes of administration.

Table 3

| Species | Route | $LD_{50}$(mg/kg) |
|---|---|---|
| Rat | p.o. | 5000 |
| | s.c. | 5000 |
| | i.v. | 1310–2560 |
| Mouse | p.c. | 5000 |
| | s.c. | 4000–5000 |
| | i.v. | 1638–2048 |

4. Anti-Mycoplasma activity

Pseudomonic acid (Na salt) and methyl pseudomonate both possess good antimycoplasmal activity in vitro against mycoplasmas from human and veterinary sources (Table 4).

Pseudomonic acid is also active in vivo in experimentally induced mycoplasmal infections in mice and chicken.

In two experiments in mice pseudomonic acid given daily at a concentration of 200 mg/kg subcutaneously for five consecutive days, prevented the development of arthritis in four out of five mice and four out of eight mice respectively (Table 5).

In chicken pseudomonic acid administered intramuscularly twice per day to *M. synoviae*-infected chicks at a dose of 200 mg/kg, prevented the development of air-sac lesions in four out of five birds. *M. synoviae* was not re-isolated from the airsacs of any of the pseudomonic acid treated chicks (Table 6).

Methods

1. The minimal inhibitory concentrations (MIC) of pseudomonic acid and methyl pseudomonate were determined in Microtitre plates, by a modification of the metabolic-inhibition test (Taylor-Robinson, 1967). The compounds were serially diluted in sterile de-ionised water to give a range of concentrations from 250-0.5 $\mu$g/ml. Mycoplasma broth containing 1% (w/v) of glucose and 0.005% (w/v) of phenon red, was added at a strength to compensate for its dilution by the aqueous drug solution. Approximately $10^4$ colony forming units of mycoplasma were added to each concentration of drug. Drug-free infected, noninfected and pH control wells were included on each plate. Plates were sealed with cellotape and incubated at 37° C. for seven days. The MIC was the lowest concentration of compound that prevented a colour change in the mycoplasma broth, caused by the metabolism of glucose by the mycoplasmas.

scopically for mycoplasmal lesions and microbiologically for the presence of M. synoviae.

References

Taylor-Robinson, 1967. Mycoplasmas of various hosts and their antibiotic sensitivities. Post. Grad. Med. J., 43 Suppl. [March], 100.

Hannan, 1977. Sodium aurothiomalate, gold keratinate and various tetracyclines in mycoplasma-induced arthritis of rodents. J. Med. Microbiol. 10, 87.

Table 4

The in vitro antimycoplasmal activities of Pseudomonic acid (Na salt) and methyl pseudomonate

| Compound | M. gallisepticum S6 | M. synoviae 25204 | M. pulmonis 'JB' | M. bovis 25025 | M. suipneumoniae (Laber) | M. dispar H225 | M. pneumoniae 427 a | M. fermentans MW KL 4 |
|---|---|---|---|---|---|---|---|---|
| Pseudomonic Acid (Na salt) | 7.8 | <0.5 | <0.5 | <0.5 | 1.9–3.9 | <0.5 | <0.5 | <0.5 |
| Methyl pseudomonate | 15.6 | <0.5 | <0.5 | <0.5 | 7.8 | <0.5 | 7.8 | <0.5 |

Table 5

Effect of pseudomonic acid on the development of M. Pulmonis-induced arthritis of mice Challenge doses M. pulmonis 'JB'   Expt 1: 5 × $10^4$CFU/mouse   Mouse strain   Expt 1 ♀ NIH (AS)
Expt 2: 5.8 × $10^3$CFU/mouse                                    Expt 2 ♀ NIH (Anglia)

| Treatment | Dose (mg/kg) | Number of mice with arthritis/total number mice at time (days after infection) | | | |
|---|---|---|---|---|---|
| | | 3 | 7 | 10 | 14 |
| Expt 1 | | | | | |
| Pseudomonic Acid | 200 × 5 s.c. | 0/6 | 1/5 | 1/5 | 1/5 |
| None (infected control) | — | 4/7 | 6/7 | 6/7 | 6/7 |
| None (non-infected control) | — | 0/8 | 0/8 | 0/8 | 0/8 |
| | | 3 | 8 | 10 | 14 |
| Expt 2 | | | | | |
| Pseudomonic acid | 200 × 5 s.c. | 0/8 | 2/8 | 2/8 | 4/8 |
| None (infected control) | — | 4/8 | 8/8 | 8/8 | 8/8 |
| None (non-infected control) | — | 0/8 | 0/8 | 0/8 | 0/8 |

2. M. pulmonis-induced arthritis of mice

The method used to induce arthritis was as described previously (Hannan 1977), M. pulmonis strain 'JB' was injected intravenously (0.5 ml) at a concentration of $10^3$–$10^5$ colony forming units per ml. (CFU/ml), into the tail veins of groups of six to eight female mice (NIH strain) each weighing between 18-22 grams. Immediately after infection and then daily for four consecutive days, the mice were dosed subcutaneously with pseudomonic acid at a concentration of 200 mg/kg. The mice were then observed at intervals for a period of two weeks for the development of arthritis in the limbs and paws.

3. M. synoviae-induced airsacculitis of chicken 0.5 ml volumes of a broth culture containing about $10^8$ CFU of M. synoviae ATCC No. 25204 were injected into the left abdominal air sacs of groups of five, one week old, specific pathogen free (SPF) white leghorn chicks. Pseudomonic acid at a concentration of 200 mg/kg was administered intramuscularly immediately after infection and then twice daily for a further three consecutive days. Seven days after infection the chicks were autopsied and the air sacs were examined macroscopically for mycoplasmal lesions and microbiological Table 6

Effect of Pseudomonic acid on the development of M. synoviae-induced airsacculitis of chickens Challenge dose: $10^8$CFU/chick   Chicks: white leghorn (Wickham Laboratories)
M. synoviae+ ATCC 25204

| Treatment | Dose (mg/kg) | Number birds protected/ total | Number of birds from which M. synoviae was re-isolated |
|---|---|---|---|
| Pseudomonic acid | 200 × 7* i.m. | 4/5 | 0 |
| None (Infected Control) | — | 0/5 | 5 |
| None (non-infected control) | — | — | 0 |

*Chicks dosed once on the day of infection and then twice daily for three consecutive days
+intra-airsac inoculation

What we claim is:

1. A method of treating respiratory and venereal diseases caused by Haemophilus and Neisseria organisms in mammals, which comprises administering to a mammal suffering from such a disease, an effective amount of pseudomonic acid of the formula (I):

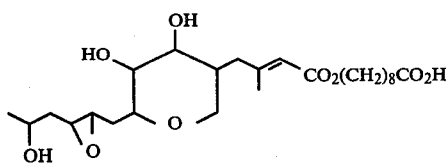
(I)

a pharmaceutically acceptable salt thereof or an alkyl ester thereof of 1-6 carbon atoms.

2. A method according to claim 1 wherein the compound administered is pseudomonic acid, an alkali metal salt or alkyl ester thereof of 1 to 6 carbon atoms.

3. A method according to claim 1 wherein the compound administered is pseudomonic acid, the sodium salt or methyl ester thereof.

4. A method according to claim 1 wherein the mammal is a human.

5. A method according to claim 1 wherein the mammal is a species of cattle, swine or poultry.

6. A method according to claim 1 wherein the administration is oral.

7. A method according to claim 1 for treating respiratory diseases in humans which comprises administering an amount of said compound sufficient to be effective against said respiratory disease.

8. A method according to claim 1 for the treatment of venereal disease in humans which comprises administering an amount of said compound sufficient to be effective against said venereal disease.

9. A method according to claim 1 of treating *N. gonorrhoeae* in mammals which comprises administering to a mammal in need thereof an anti-*N. gonorrhoeae* effective amount of said pseudomonic acid or a pharmaceutically acceptable salt or pharmaceutically acceptable ester thereof.

* * * * *